(12) United States Patent
Sakamoto (10) Patent No.: US 8,562,347 B2
(45) Date of Patent: Oct. 22, 2013

(54) DENTAL IMPLANTS

(75) Inventor: Yuki Sakamoto, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 13/242,930

(22) Filed: Sep. 23, 2011

(65) Prior Publication Data

US 2012/0082956 A1    Apr. 5, 2012

(30) Foreign Application Priority Data

Sep. 30, 2010   (JP) ................................ 2010-220572

(51) Int. Cl.
*A61C 8/00* (2006.01)
(52) U.S. Cl.
USPC ........................................................ 433/173
(58) Field of Classification Search
USPC ..................... 433/172–176, 201.1; 623/17.17
See application file for complete search history.

(56) References Cited

U.S. PATENT DOCUMENTS

| | | | | |
|---|---|---|---|---|
| 5,302,126 A | * | 4/1994 | Wimmer et al. | 433/173 |
| 5,350,302 A | * | 9/1994 | Marlin | 433/174 |
| 5,376,004 A | * | 12/1994 | Mena | 433/173 |
| 5,782,918 A | * | 7/1998 | Klardie et al. | 606/60 |
| 6,168,436 B1 | * | 1/2001 | O'Brien | 433/173 |
| 7,014,464 B2 | * | 3/2006 | Niznick | 433/173 |
| 7,344,376 B2 | * | 3/2008 | Beaty et al. | 433/173 |
| 2008/0241793 A1 | * | 10/2008 | Collins et al. | 433/174 |

FOREIGN PATENT DOCUMENTS

| | | |
|---|---|---|
| CA | 2351434 A1 * | 7/2000 |
| DE | 203 03 653 U1 | 4/2004 |
| FR | 2 747 031 | 10/1997 |
| JP | 2004-113718 | 4/2004 |
| JP | 2005-329244 | 12/2005 |
| WO | WO 99/16293 | 4/1999 |
| WO | WO 2008/071368 A1 | 6/2008 |

OTHER PUBLICATIONS

Extended European Search Report issued Dec. 6, 2011, in Application No. / Patent No. 11007884.7-1269.

* cited by examiner

*Primary Examiner* — Cris L Rodriguez
*Assistant Examiner* — Edward Moran
(74) *Attorney, Agent, or Firm* — Oblon, Spivak, McClelland, Maier & Neustadt, L.L.P.

(57) ABSTRACT

A dental implant has a dental implant fixture with a fitting hole at the oral cavity-side end, and an abutment with a fitting portion at one end which is to be fitted, not to be rotatable, in the fitting hole in the dental implant fixture.

The dental implant fixture has at a side of the fitting hole opposite to the oral cavity an internal thread with which external threads formed on a cover screw and healing abutment are to be put into engagement. The abutment has a truncated-conical gum piercing portion with a cross section which is larger in area as it goes away from the fitting portion, and a columnar portion which is not circular in cross section and to which a dental prosthesis fixing device is to be attached. The fitting portion has an internal thread smaller in inside diameter than that in the dental implant fixture.

13 Claims, 7 Drawing Sheets

DENTAL IMPLANTS

BACKGROUND OF THE INVENTION

1. Field of the Invention

The present invention relates to a dental implant including a dental implant fixture and an abutment fitted and fixed in the dental implant fixture, only the abutment being removable for replacement while the dental implant fixture is being left fitted and fixed in place in an implanting hole made in the jawbone even at occurrence of a trouble such as damage to a broken dental prosthesis, fracture of a portion of the abutment to which the dental prosthesis is fixed or the like.

2. Description of the Conventional Art

In the field of dental therapy, there have been developed dental implant techniques in which an implanting hole is formed in a portion of the jawbone where a natural tooth is missing, a dental implant fixture to keep a dental prosthesis is placed in the implanting hole to work instead of the root of a natural tooth, an abutment as a first upper structural member is installed directly to the oral cavity-side end of the dental implant fixture, a dental prosthesis fixing device as a second upper structural member is fixed to the abutment to provide a dental prosthesis retaining device and a dental prosthesis is attached to the dental prosthesis retaining device.

As one of the dental treatment techniques, there is mainly adopted a dental implanting method called "two-stage process". In this method, the following is done:

a dental implant fixture is placed in an implanting hole formed in a portion of the jawbone where a natural tooth is missing;

the oral cavity-side end of the dental implant fixture is covered with a cover screw;

the gingival flap having been cut out for drilling the implanting hole in the jawbone is stitched closed;

a certain healing period is set for which an integration of the dental implant fixture with the surrounding bone, called "osseointegration", will be attained so that the dental implant fixture will be sufficiently integrated with the jawbone portion corresponding to the missing tooth and the gum tissue cut out for forming the implanting hole will heal;

after completion of the healing period, it is checked that the dental implant fixture is sufficiently integrated with the jawbone and the gum tissue has healed;

an incision is made again in an oral cavity-side portion of the gum tissue in which the dental implant fixture is placed and the cover screw is removed;

a healing abutment is installed to the oral-cavity end of the dental implant fixture;

a hole is made and kept in the gum for fixing through it an abutment as a first upper structural member having a portion on which a dental prosthesis fixing device is to be mounted;

another healing period for which the gum will heal is set; after completion of this healing time, it is checked that the gum has healed; and the abutment is finally fixed in the hole.

Recently, in addition to the above-mentioned two-stage process, there has also become employed a dental implanting method called "single-stage process" in which immediately after a dental implant fixture is placed in an implanting hole formed in a jawbone portion where a natural tooth is missing, a healing abutment or an abutment is installed to the oral cavity-side end of the dental implant fixture. Namely, no surgery is done for exteriorizing the cover screw as at the second stage of the two-stage process. This one-stage process has been adopted more and more because both the patient and dental surgeon bear less; however, it has a high risk for infection in case bone argumentation is required because the jawbone is not enough in height and thickness to place a dental implant.

Both the above processes (especially the two-stage process) frequently use a dental implant fixture which is internally threaded and an abutment which is externally threaded. Namely, the abutment is fixed to the dental implant fixture by threading the former into the latter. Such a technique is disclosed in the Japanese Published Unexamined Application No. 113718 of 2004, for example. For such fixing of the abutment to the dental implant fixture by threading, however, a through-hole for a fixation screw has to be formed in the abutment. Especially, in case the abutment used is an order-made one manufactured with the use of a CAD/CAM system, designing such an order-made abutment is limited by the necessity of the through hole for the fixation screw. Particularly, in case the dental prosthesis fixing device as a second upper structural member to be fixed to the abutment has a small external form, the portion of the abutment to which the dental prosthesis fixing device is to be fixed should be thin. Also, if priority is given to forming the through hole for the fixation screw, the abutment cannot be formed to have any portion large enough to receive and fix the dental prosthesis fixing device. Further, even if it is barely possible to design an abutment having a portion to which the dental prosthesis fixing device can be fixed, the dental prosthesis cannot be formed sufficiently thick in many cases. Consequently, there are problems that no satisfactory strength and color can be imparted to the dental prosthesis.

Also, there has been proposed an integral type dental appliance formed from an integration of a dental implant fixture and abutment. This is disclosed in the Japanese Published Unexamined Application No. 329244 of 2005, for example. Also in the dental appliance of such an integral type, however, a portion of the dental appliance corresponding to the abutment to which the dental prosthesis fixing device is to be fixed cannot be formed thin since it is necessary to form, in the abutment portion of the dental appliance, a relatively large engagement hole in which there is to be inserted a tool for placing the dental appliance in an implanting hole formed in a jawbone portion corresponding to a missing tooth. Even if it is barely possible to form a thin portion of the dental appliance corresponding to the abutment, the dental prosthesis cannot be designed sufficiently thick many cases. Thus, there remains unsolved a problem that no satisfactory strength and color can be imparted to the dental prosthesis. Also, the integral type dental appliance is seriously disadvantageous in that at occurrence of a trouble such as damage to a dental prosthesis fixed to a dental prosthesis fixing device, fracture of a portion of the appliance to which the dental prosthesis fixing device is to be fixed or the like in the process of an implant surgery in which the dental prosthesis fixing device fixed to the integrated type dental appliance is used as a dental prosthesis retaining device and the dental prosthesis is fixed to the dental prosthesis fixing device, the dental appliance itself becomes unusable and another implant surgery has to be retried from the beginning.

SUMMARY OF THE INVENTION

It is therefore desirable to overcome the above-mentioned drawbacks of the prior art by providing a dental implant of which the abutment cannot only be formed to have a thin portion to which a dental prosthesis fixing device is to be fixed so that a dental prosthesis can be designed with increased freedom but also only the abutment can be removed for replacement while the dental implant fixture is being left fitted and fixed in place in an implanting hole in the jawbone even at occurrence of a trouble such as damage to a dental prosthesis, fracture of a portion of the abutment to which the dental prosthesis fixing device or the like.

The Inventor of the present invention has devoted himself to solve the above-mentioned problems. As the result, he has worked out a dental implant including a dental implant fixture having formed therein at the oral cavity-side end thereof a fitting hole in which an abutment is to be fitted not to be rotatable and thereon at the side of the fitting hole opposite to the oral cavity an internal thread with which external threads formed on a cover screw and healing abutment are to be put into engagement, the abutment having a fitting portion formed at one end thereof and which is to be fitted, not to be rotatable, in the fitting hole in the dental implant fixture, a truncated-conical gum piercing portion formed at the other end thereof to have a cross section which is larger in area as it goes away from the fitting portion, and a columnar portion which is not circular in cross section and to which a dental prosthesis fixing device is to be attached, the fitting portion having formed therein an internal thread smaller in inside diameter than that in the dental implant fixture. Owing to the above design, this dental implant can be used as follows:

First an implanting hole is drilled in a portion of the jawbone corresponding to a missing tooth. The dental implant fixture is placed in the implanting hole. Then, the external thread formed on the cover screw is put into engagement with the internal thread of the dental implant fixture placed as above to cover the cavity-side end of the dental implant fixture, and then the gingival flap having been cut out is stitched closed. A certain healing period of time is set for which an integration of the dental implant fixture with the surrounding bone, called "osseointegration", will be attained so that the dental implant fixture will be satisfactorily integrated with the jawbone portion corresponding to the missing tooth and the gum tissue having been cut out for forming the implanting hole will heal. After completion of the healing period, it is checked that the dental implant fixture is satisfactorily integrated with the jawbone and the gum tissue has healed, an incision is made again in an oral cavity-side portion of the gum tissue in which the dental implant fixture is placed, the cover screw is removed. Then, by putting the external thread formed on the healing abutment into engagement with the internal thread formed in the dental implant fixture, the healing abutment is installed to the oral cavity-side end of the dental implant fixture to ensure a hole through which the abutment as a first upper structural member is fixed. Another healing period of time is set for which the gum tissue will have healed. When this healing time is over and the gum is found healed, the healing abutment is removed and the fitting portion of the abutment is fitted, not to be rotatable, into the fitting hole in the dental implant fixture.

Namely, a dental implant which can be used successfully just by fitting the abutment into the oral cavity-side end of the dental implant fixture has been worked out. The columnar portion of the abutment, which projects into the oral cavity from the dental implant fixture and to which the dental prosthesis fixing device is to be attached, can be formed thin. Thus the dental prosthesis can be designed with increased freedom. In addition, even at occurrence of a trouble such as damage to the dental prosthesis, fracture of the columnar portion of the abutment to which the dental prosthesis fixing device is to be attached or the like, only the abutment can be removed for replacement while the dental implant fixture being left fixed in place in the implanting hole in the jawbone. The abutment can be so removed by grinding away the dental prosthesis and columnar portion of the abutment, and then the gum piercing portion to such an extent that the internal thread formed in the fitting portion of the abutment becomes exposed, threading an abutment extracting tool into the fitting portion of the abutment from inside the oral cavity with an external thread formed on the tool being put in engagement with the internal thread in the fitting portion until the free end thereof abuts the bottom of the internal thread of the dental implant fixture, and making further turning of the tool, which allows the abutment to come out of the fitting hole in the dental implant fixture.

According to the present invention, there is provided a dental implant including a dental implant fixture having formed therein at the oral cavity-side end thereof a fitting hole in which an abutment is to be fitted not to be rotatable and thereon at the side of the fitting hole opposite to the oral cavity an internal thread with which external threads formed on a cover screw and healing abutment are to be put into engagement, the abutment having a fitting portion formed at one end thereof and which is to be fitted, not to be rotatable, in the fitting hole in the dental implant fixture, a truncated-conical gum piercing portion formed at the other end thereof to have a cross section which is larger in area as it goes away from the fitting portion, and a columnar portion which is not circular in cross section and to which a dental prosthesis fixing device is to be attached, the fitting portion having formed therein an internal thread smaller in inside diameter than that in the dental implant fixture.

As mentioned above, the dental implant according to the present invention includes a dental implant fixture having formed therein at the oral cavity-side end thereof a fitting hole in which an abutment is to be fitted not to be rotatable and thereon at the side of the fitting hole opposite to the oral cavity an internal thread with which external threads formed on a cover screw and healing abutment are to be put into engagement, the abutment having a fitting portion formed at one end thereof and which is to be fitted, not to be rotatable, in the fitting hole in the dental implant fixture, a truncated-conical gum piercing portion formed at the other end thereof to have a cross section which is larger in area as it goes away from the fitting portion, and a columnar portion which is not circular in cross section and to which a dental prosthesis fixing device is to be attached, the fitting portion having formed therein an internal thread smaller in inside diameter than that in the dental implant fixture. Owing to the design of the dental implant according to the present invention, it is possible to fix the cover screw and healing abutment with the internal thread in the dental implant fixture once placed in the implanting hole formed in a jawbone portion where a natural tooth is missing. Thus, the dental implant according to the present invention is successfully usable in the dental implant surgery employing the two-stage process. Additionally, since the abutment can easily fixed to the dental implant fixture just by fitting it, not to be rotatable, into the fitting hole formed in the oral cavity-side end of the dental implant fixture, it is possible to form a thin columnar portion of the abutment, which projects into the oral cavity from the dental implant fixture and to which the dental prosthesis fixing device is to be attached. That is, the dental prosthesis can be designed with increased freedom. Further, even at occurrence of a trouble such as damage to the dental prosthesis, fracture of the columnar portion of the abutment to which the dental prosthesis fixing device is to be attached or the like, only the abutment can be removed for replacement with the dental implant fixture being left fixed in place in the implanting hole in the jawbone. The abutment can be so removed by grinding away the dental prosthesis and columnar portion of the abutment and then the gum piercing portion to such an extent that the internal thread formed in the fitting portion of the abutment becomes exposed, threading an abutment extracting tool into the fitting portion of the abutment from inside the oral cavity with an external thread formed on the tool being put in engagement with the internal thread in the fitting portion until the free end of the abutment extracting tool abuts the bottom of the internal thread of the dental implant fixture, and making further turning of the tool, which allows the abutment to come out of the fitting hole in the dental implant fixture.

The foregoing and other features, aspects and advantages of the present invention will become more apparent from the following detailed description of embodiments of the present invention when taken in conjunction with the accompanying drawings. It should be noted that the present invention is not limited to the embodiments but can freely be modified without departing from the scope and spirit thereof defined in the claim given later.

DETAILED DESCRIPTION OF THE PREFERRED EMBODIMENTS

The present invention will be described in detail below concerning the preferred embodiments thereof with reference to the accompanying drawings.

As shown, the dental implant according to the present invention includes a dental implant fixture 1 as one of the components thereof. The dental implant fixture 1 has formed at a dental cavity-side end thereof a fitting hole 1a in which an abutment 2 which will be described in detail later is to be fitted not to be rotatable, and on a side of the fitting hole 1a opposite to the oral cavity an internal thread 1b in which an external thread formed on a cover screw and healing abutment are to be threaded.

Figure 1:
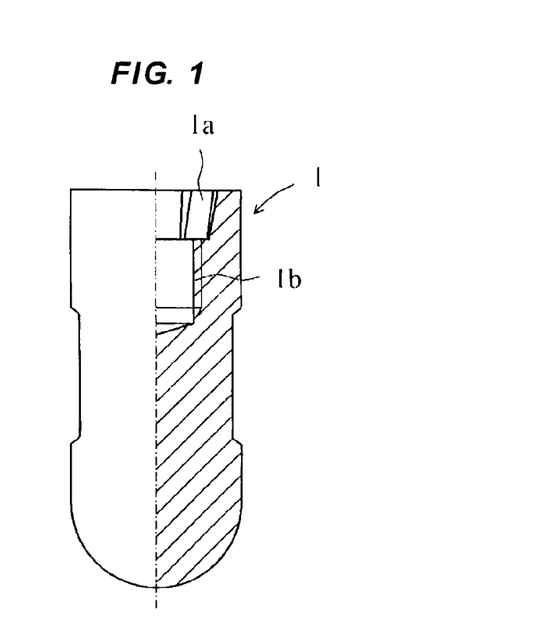
FIG. 1 is a side elevation of one embodiment of the dental implant fixture as one component of the dental implant according to the present invention, showing the right half of the fixture in section.
Figure 3:
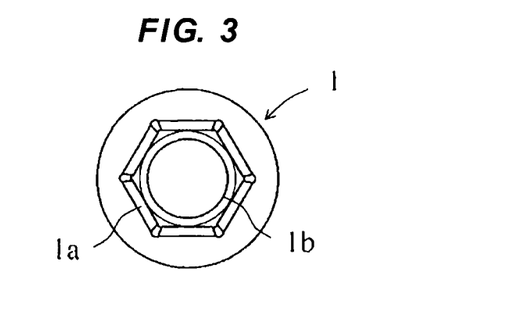
FIG. 3 is a plan view of the dental implant fixture shown in FIG. 1.
Figure 6:
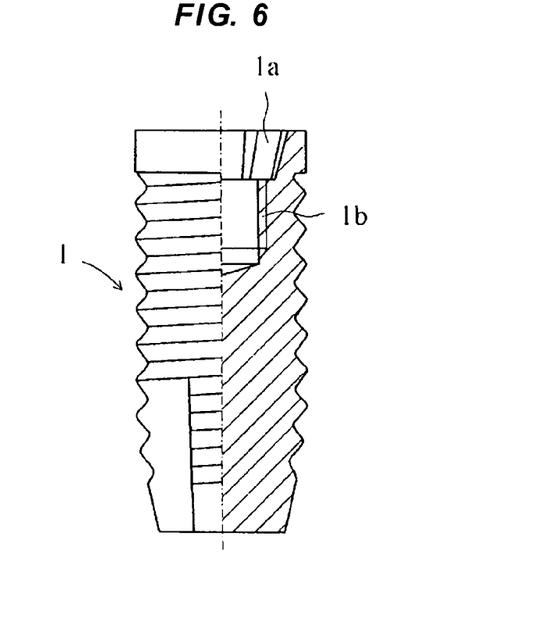
FIG. 6 is a side elevation of another embodiment of the dental implant fixture as the one component of the dental implant according to the present invention, showing the right half of the fixture in section.
Figure 8:
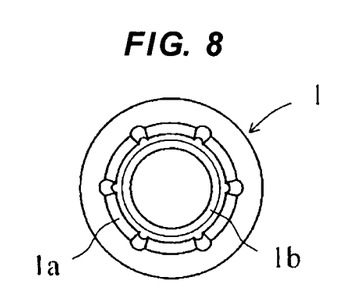
FIG. 8 is a plan view of the dental implant fixture shown in FIG. 6.

There are various embodiments of the cross-sectional shape of the fitting hole 1a such as hexagonal as shown in FIGS. 1 and 3, and circular as shown in FIGS. 6 and 8. In the latter case, concave engagement grooves are formed at predetermined intervals along the circumference of the fitting hole 1a. In any embodiments, the fitting hole 1a is tapered to be narrower as it goes from the oral cavity-side end toward the free end of the dental implant fixture 1.

The dental implant fixture 1 may be of a tap-in type as in the embodiment which will be explained below with reference to FIGS. 1 and 3 or of a self-tap type as in the embodiment which will be explained with reference to FIGS. 6 and 8.

As shown, the dental implant according to the present invention includes also the abutment 2. At one end of the abutment 2 there is formed a fitting portion 2a which is to be fitted, not to be rotatable, in the fitting hole 1a formed in the dental implant fixture 1. The fitting portion 2a is contiguous at the other end thereof to a truncated-conical gum piercing portion 2b of which the cross section is larger in area as it goes away from the fitting portion 2a, and the gum piercing portion 2b is further contiguous to a columnar portion 2c having a noncircular cross section and to which the dental prosthesis fixing device is to be attached. Further, the fitting portion 2a has formed on the inner wall thereof an internal thread 2d of which the inside diameter is smaller than that of the internal thread 1b of the dental implant fixture 1.

Figure 2:
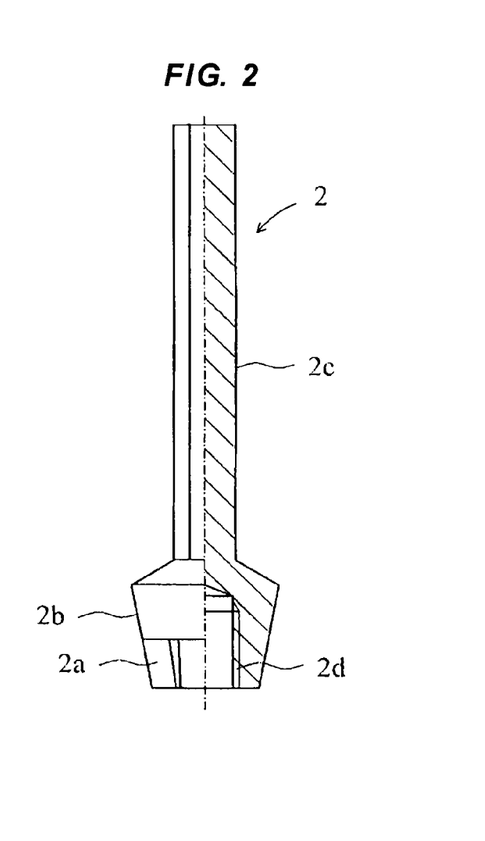
FIG. 2 is also a side elevation of one embodiment of the abutment as the other component of the dental implant according to the present invention, showing the right half of the abutment in section.
Figure 4:
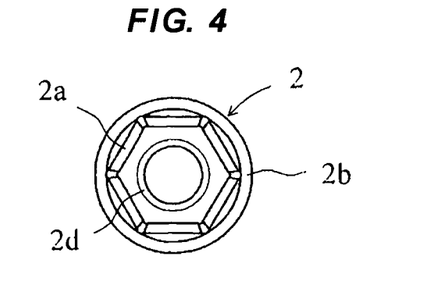
FIG. 4 is a bottom view of the abutment shown in FIG. 2.
Figure 5:
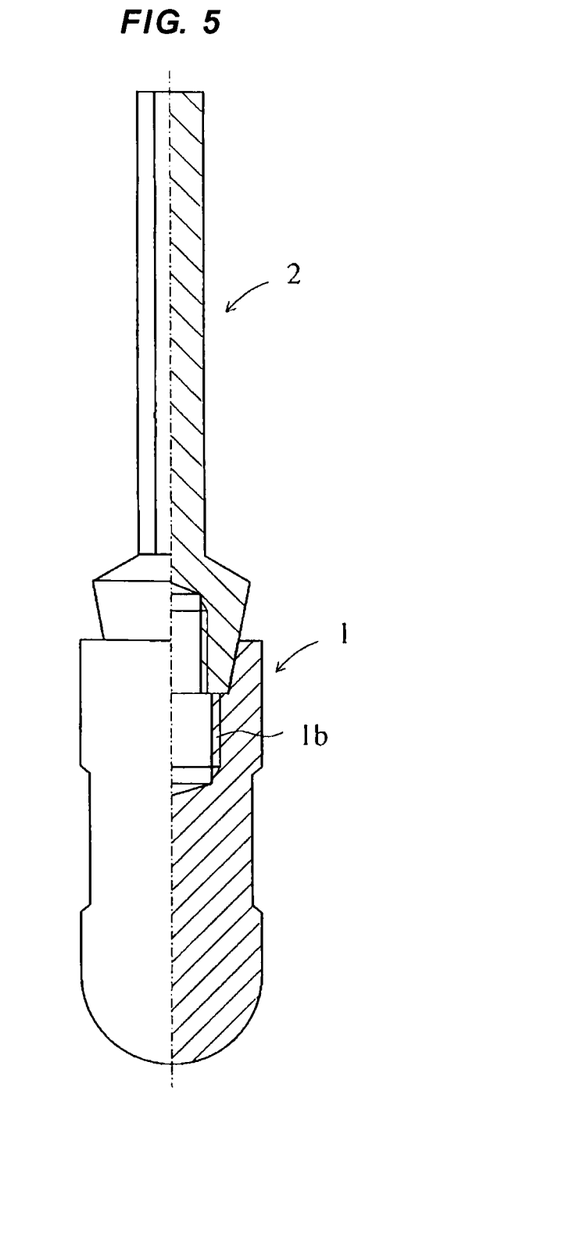
FIG. 5 is a sectional view of the dental implant according to the present invention, explaining how the components shown in FIGS. 1 to 4 are assembled together to build the dental implant according to the present invention.
Figure 7:
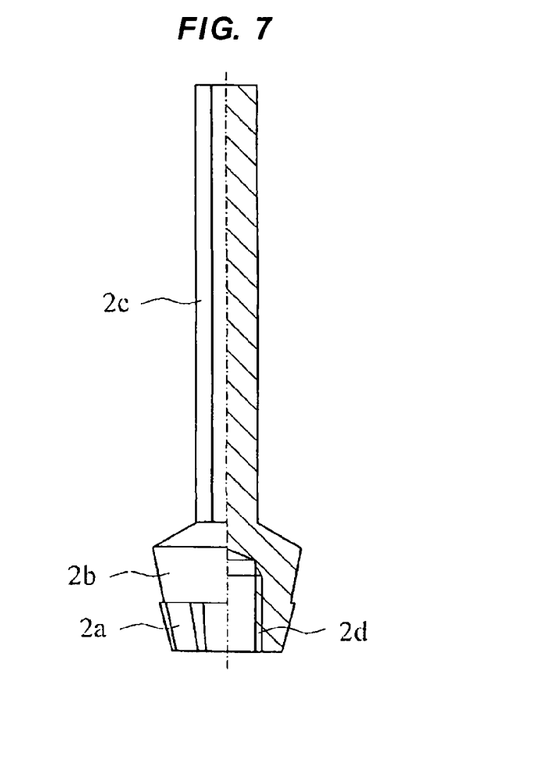
FIG. 7 is also a side elevation of another embodiment of the abutment as the other component of the dental implant according to the present invention, showing the right half of the abutment in section.
Figure 9:
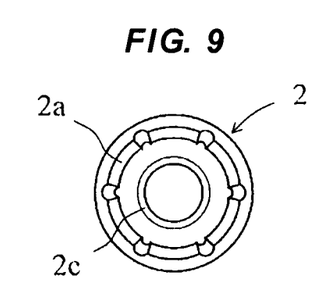
FIG. 9 is a bottom view of the abutment shown in FIG. 7.
Figure 10:
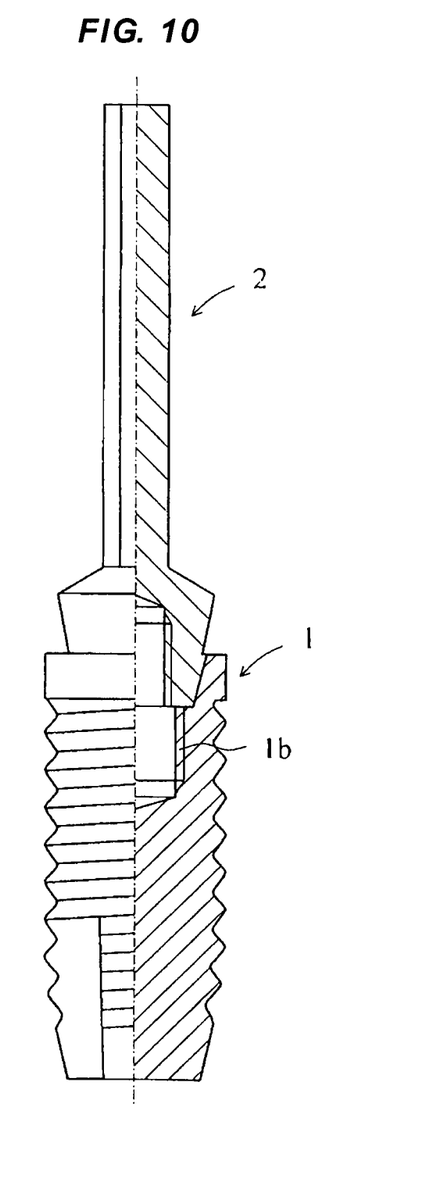
FIG. 10 is a sectional view of the dental implant according to the present invention, explaining how the components shown in FIGS. 6 to 9 are assembled together to build the dental implant according to the present invention.

In case the fitting hole 1a in the dental implant fixture 1 has a hexagonal cross section as shown in FIGS. 1 and 3, the fitting portion 2a of the abutment 2 may be externally shaped as a hexagonal cylinder as shown in FIGS. 2 and 4. Also, in case the fitting hole 1a in the dental implant fixture 1 is circular in cross section and has concave engagement grooves formed at predetermined intervals along the circumference thereof as shown in FIGS. 6 and 8, the fitting portion 2a may be externally shaped as a cylindrical column to have convexities formed at predetermined intervals along the circumference of the column as shown in FIGS. 7 and 9. In any case, the fitting portion 2a is tapered to be smaller in cross sectional area as it goes away from the gum piercing portion 2b.

Further, the columnar portion 2c not circular in cross section and to which the dental prosthesis fixing device is to be attached may be formed directly contiguous to the gum piercing portion 2b of which the cross sectional area increases as it goes away from the fitting portion 2a. It should be noted however that the columnar portion 2c may be contiguous to the gum piercing portion 2b via the truncated-conical portion of which the cross sectional area decreases as it goes away from the gum piercing portion 2b as shown in FIGS. 2, 4, 7 and 9.

Figure 11:
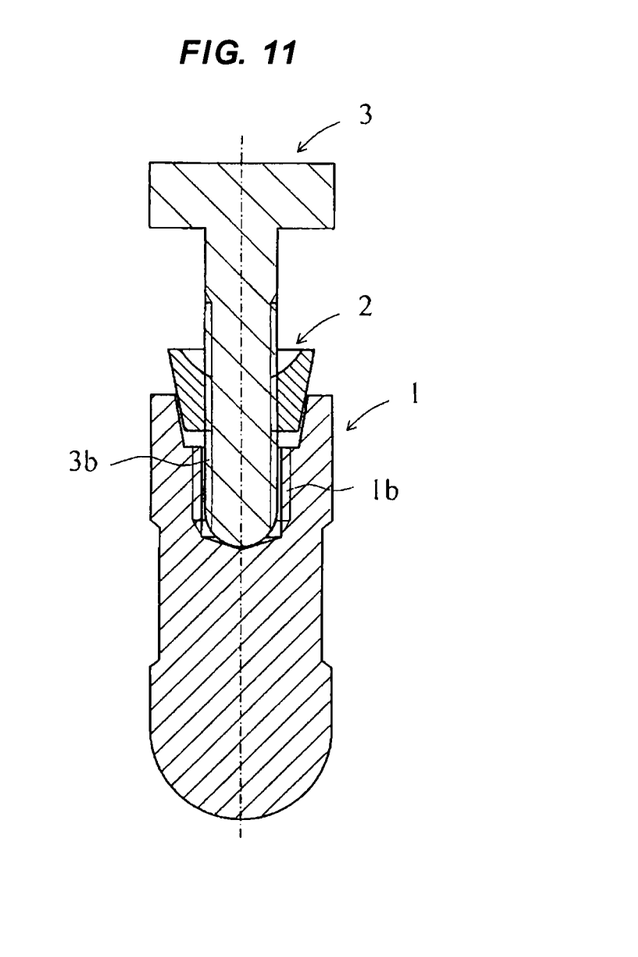
FIG. 11 explains how the abutment can be taken out of the fitting hole at occurrence of a trouble such as damage to the dental prosthesis, fracture of a columnar portion of the abutment to which the dental prosthesis fixing device is attached or the like; the removal of the abutment being attainable by grinding away the gum piercing portion until the internal thread formed in the abutment fitting portion becomes exposed and threading an abutment extracting tool into the fitting hole as shown.

In FIG. 11, the reference numeral 3 indicates an abutment extracting tool. The abutment extracting tool 3 is to be used to remove the abutment for replacement if there occurs a trouble such as damage to a dental prosthesis, fracture of the columnar portion 2c of the abutment 2 to which the dental prosthesis fixing device is attached or the like when the dental implant is being used with the fitting portion 2a of the abutment 2 being fitted in the fitting hole 1a in the dental implant fixture 1 and the dental prosthesis fixing device being attached on the columnar portion 2c of the abutment 2. With this abutment extracting tool 3, it is possible to remove only the abutment 2 with the dental implant fixture being left fixed in place in the implanting hole formed in the jawbone. The abutment extraction tool 3 has formed at the free end thereof an external thread 3a which is to be put into engagement with the internal thread 2d formed in the fitting portion 2a of the abutment 2.

In an implant surgery using the dental implant including the dental implant fixture 1 and abutment 2 according to the present invention, an implanting hole is first formed in a jawbone portion corresponding to a missing tooth, and the dental implant fixture 1 is then placed into the implanting hole. In this implant placement, an implanting tool (not shown) is put at the free end thereof into the fitting hole 1a formed at the oral cavity-side end of the dental implant fixture 1. In case the dental implant fixture 1 is of a tap-in type as in the embodiment shown in FIGS. 1 and 3, the implanting tool is tapped at the other end thereof opposite to the dental implant fixture 1. Otherwise, in case the dental implant fixture 1 is of a self-tap type as in the embodiment shown in FIGS. 6 and 8, the implanting tool is rotated.

Once the dental implant fixture 1 is thus placed in the implanting hole formed in the portion of the jawbone corresponding to the missing tooth, the external thread formed on a cover screw (not shown) is put into engagement with the internal thread 1b in the dental implant fixture 1. The oral cavity-side end of the dental implant fixture 1 is covered with the cover screw. Then, the gingival flap having been cut out is stitched closed. A certain healing period of time is set. After completion of the set period of time, it is checked that an integration of the dental implant fixture 1 with the surrounding bone, called "osseointegration", has been so attained that the dental implant fixture 1 is satisfactorily integrated with the jawbone portion corresponding to the missing tooth and the gum tissue cut out for forming the implanting hole has healed. Then, an incision is made again in the gum portion at the oral cavity side in which the dental implant fixture is placed, and the cover screw is removed from there. By putting the external thread formed on the healing abutment (not shown) into engagement with the internal thread 1b of the dental implant fixture 1, the healing abutment is installed to the oral cavity-side end of the dental implant fixture 1 to ensure a hole through which the abutment 2 as the first upper structural member is fixed. With confirmation that the gum has healed, the healing abutment is removed. Then, the fitting portion 2a of the abutment 2 is fitted, not to be rotatable, in the fitting hole 1a in the dental implant fixture 1.

After that, a hole in the dental prosthesis fixing device, corresponding to the columnar portion 2a of the abutment 2, is aligned with the columnar portion 2c of the abutment 2, and the fixing device is fixed to the columnar portion 2c with a dental adhesive such as cement or the like. It should be noted that the dental prosthesis fixing device is formed from a block of ceramic or alloy by automatic cutting work with a CAD/CAM system.

In this process, the columnar portion 2c of the abutment 2, which projects into the oral cavity from the dental implant fixture 1 and to which the dental prosthesis fixing device is to be attached, can be formed sufficiently thinner than the portion of the abutment 2 to which a conventional dental prosthesis fixing device is to be attached, and thus the dental prosthesis fixing device can be designed smaller. Therefore, the dental prosthesis fixing device can be designed with increased freedom. As the result, coping can be formed thicker so that color matching of the dental prosthesis can be done more easily.

Also, even at occurrence of a trouble such as damage to the dental prosthesis, fracture of the columnar portion 2c of the abutment 2 to which the dental prosthesis fixing device is to be attached or the like, only the abutment 2 can be removed for replacement while leaving the dental implant fixture 1 fixed in place in the implanting hole in the jawbone. To remove the abutment 2 as above, the dental prosthesis and columnar portion 2c of the abutment 2 are ground away and the gum piercing portion 2b is ground away to such an extent that the internal thread 2d formed in the fitting portion 2a of the abutment 2 becomes exposed, then the abutment extracting tool 3 is screwed from inside the oral cavity into the fitting portion 2a of the abutment 2 with an external thread 3a formed on the tool 3b being put in engagement with the internal thread 2d formed in the fitting portion 2a until the free end of the abutment extracting tool 3 abuts the bottom of the internal thread 1b of the dental implant fixture 1, and the abutment extracting tool 3 is turned, as shown in FIG. 11. Turning the tool 3 allows the abutment 2 to come out of the fitting hole 1a in the dental implant fixture 1.

What is claimed is:

1. A dental implant, comprising:
   a dental implant fixture having a fitting hole formed therein at an oral cavity-side end, the fitting hole having an internal thread formed thereon at a side of the fitting hole opposite to the oral cavity; and
   an abutment having:
      a fitting portion having an upper/proximal end and a lower/distal end, wherein the upper end is closer to the oral cavity than the lower end, and wherein the lower end is disposed at a first end of the abutment and the lower end fits, without being rotatable, in the fitting hole of the dental implant fixture;
      a truncated-conical gum piercing portion proximal to the upper end of the fitting portion, which is opposite the lower end of the fitting portion, and has a cross section that increases in area with distance away from the fitting portion; and
      a columnar portion, which is not circular in cross section, disposed at a second end of the abutment, wherein the first end of the abutment is opposite the second end of the abutment,
   wherein the lower end of the fitting portion has an internal thread formed therein, which is smaller in inside diameter than the internal thread in the dental implant fixture the two threads being coaxial, and wherein the columnar portion and the gum piercing portion are capable of being ground away to allow an extraction tool to be engaged with the internal thread in the fitting portion of the abutment.

2. The dental implant of claim 1, wherein the fitting hole is tapered to be narrower with distance away from the oral cavity-side end of the dental implant fixture.

3. The dental implant of claim 1, wherein the fitting portion is tapered to have a smaller cross sectional area with distance away from the gum piercing portion.

4. The dental implant of claim 2, wherein the fitting portion is tapered to have a smaller cross sectional area with distance away from the gum piercing portion.

5. The dental implant of claim 4, wherein the dental implant fixture is a tap-in fixture.

6. The dental implant of claim 4, wherein the dental implant fixture is a self-tap fixture.

7. The dental implant of claim 4, wherein the fitting hole of the dental implant fixture has a hexagonal cross section.

8. The dental implant of claim 7, wherein the fitting portion of the abutment has a hexagonal cross section.

9. The dental implant of claim 8, wherein the fitting portion is contiguous with the truncated-conical gum piercing portion.

10. The dental implant of claim 8, wherein the truncated-conical gum piercing portion is contiguous with the columnar portion.

11. The dental implant of claim 9, wherein the truncated-conical gum piercing portion is contiguous with the columnar portion.

12. The dental implant of claim 4, wherein the fitting hole of the dental implant fixture has a circular cross section and comprises concave engagement grooves at predetermined intervals along the circumference of the fitting hole.

13. The dental implant of claim 4, wherein the fitting portion of the abutment is fitted in the fitting hole of the dental implant fixture.

\* \* \* \* \*